(12) United States Patent
Katase

(10) Patent No.: US 9,347,901 B2
(45) Date of Patent: May 24, 2016

(54) LIQUID TRANSPORT APPARATUS AND BUBBLE DETERMINATION METHOD

(71) Applicant: SEIKO EPSON CORPORATION, Tokyo (JP)

(72) Inventor: Makoto Katase, Azumino (JP)

(73) Assignee: SEIKO EPSON CORPORATION, Tokyo (JP)

( * ) Notice: Subject to any disclaimer, the term of this patent is extended or adjusted under 35 U.S.C. 154(b) by 242 days.

(21) Appl. No.: 14/063,488

(22) Filed: Oct. 25, 2013

(65) Prior Publication Data
US 2014/0116110 A1  May 1, 2014

(30) Foreign Application Priority Data
Oct. 30, 2012  (JP) ................................ 2012-239399

(51) Int. Cl.
| | |
|---|---|
| *G01N 27/02* | (2006.01) |
| *G01N 7/00* | (2006.01) |
| *G01N 33/497* | (2006.01) |
| *G01N 33/18* | (2006.01) |
| *F04B 19/00* | (2006.01) |
| *F04B 43/12* | (2006.01) |
| *A61M 5/142* | (2006.01) |
| *A61M 5/168* | (2006.01) |
| *A61M 5/36* | (2006.01) |

(52) U.S. Cl.
CPC ........... *G01N 27/02* (2013.01); *A61M 5/14228* (2013.01); *A61M 5/14248* (2013.01); *A61M 5/16831* (2013.01); *A61M 5/16854* (2013.01); *A61M 5/365* (2013.01); *F04B 19/006* (2013.01); *F04B 43/123* (2013.01); *F04B 43/1223* (2013.01)

(58) Field of Classification Search
None
See application file for complete search history.

(56) References Cited

U.S. PATENT DOCUMENTS

| | | | | |
|---|---|---|---|---|
| 4,723,129 A | * | 2/1988 | Endo et al. | 347/56 |
| 5,723,773 A | * | 3/1998 | Bryan | 73/61.75 |
| 7,328,982 B2 | * | 2/2008 | Kusakari | 347/68 |
| 7,704,401 B2 | * | 4/2010 | Ike et al. | 210/748.15 |
| 7,874,651 B2 | * | 1/2011 | Suzuki | 347/68 |
| 8,011,759 B2 | * | 9/2011 | Sugahara | 347/55 |
| 8,303,275 B2 | * | 11/2012 | Miyazaki | A61M 5/14228 417/477.1 |
| 8,357,274 B2 | * | 1/2013 | Marquant et al. | 204/403.01 |

(Continued)

FOREIGN PATENT DOCUMENTS

| | | |
|---|---|---|
| JP | A-2000-140092 | 5/2000 |
| JP | A-2006-263018 | 10/2006 |

(Continued)

OTHER PUBLICATIONS

Apr. 2, 2015 Office Action issued in U.S. Appl. No. 14/063,447.

(Continued)

*Primary Examiner* — Peter Macchiarolo
*Assistant Examiner* — Jermaine Jenkins
(74) *Attorney, Agent, or Firm* — Oliff PLC

(57) ABSTRACT

A liquid transport apparatus includes a tube for transporting a liquid, plural fingers that push and block the tube, a cam that pushes the fingers in sequence so as to squeeze the tube to transport the liquid, a first electrode and a second electrode that are provided at the tube located further toward the downstream side than a region pushed by the plural fingers, and a determination unit that determines the presence/absence of a bubble on the basis of the impedance between the first electrode and the second electrode.

6 Claims, 16 Drawing Sheets

(56) References Cited

U.S. PATENT DOCUMENTS

| | | | | |
|---|---|---|---|---|
| 8,408,070 | B2* | 4/2013 | Matzen | 73/861.12 |
| 8,491,283 | B2* | 7/2013 | Miyazaki | F04B 43/082 417/474 |
| 8,491,284 | B2* | 7/2013 | Miyazaki | A61M 5/14228 417/474 |
| 8,491,286 | B2* | 7/2013 | Miyazaki | A61M 5/14228 417/474 |
| 8,872,527 | B2* | 10/2014 | Sturmer et al. | 324/664 |
| 8,926,297 | B2* | 1/2015 | Miyazaki | F04B 43/12 417/474 |
| 8,961,156 | B2* | 2/2015 | Katase | F04B 43/082 417/474 |
| 2008/0058703 | A1 | 3/2008 | Subramony et al. | |
| 2009/0062720 | A1 | 3/2009 | Anderson et al. | |
| 2010/0080720 | A1 | 4/2010 | Miyazaki et al. | |
| 2012/0215163 | A1 | 8/2012 | Hanson et al. | |
| 2014/0190830 | A1* | 7/2014 | Sturmer et al. | 204/452 |

FOREIGN PATENT DOCUMENTS

| | | |
|---|---|---|
| JP | A-2010-075539 | 4/2010 |
| JP | A-2010-075540 | 4/2010 |
| JP | A-2010-077947 | 4/2010 |

OTHER PUBLICATIONS

Office Action issued in U.S. Appl. No. 14/063,477 dated Sep. 12, 2014.

U.S. Appl. No. 14/063,447, filed Oct. 25, 2013 in the name of Katase.

Aug. 24, 2015 Office Action issued in U.S. Appl. No. 14/063,447.

Jan. 6, 2016 Office Action issued in U.S. Appl. No. 14/063,447.

\* cited by examiner

LIQUID TRANSPORT APPARATUS AND BUBBLE DETERMINATION METHOD

BACKGROUND

1. Technical Field

The present invention relates to a liquid transport apparatus and a bubble determination method.

2. Related Art

As a liquid transport apparatus that transports a liquid, a micro pump described in JP-A-2010-77947 is known. In the micro pump, plural fingers are arranged along a tube, and as a cam sequentially pushes the fingers, the tube is squeezed to transport the liquid.

The present inventor has discovered a phenomenon in which, when the tube is squeezed by the plural fingers to transport the liquid, bubbles are generated with the operation of the plural fingers.

SUMMARY

An advantage of some aspects of the invention is to discriminate the presence/absence of a bubble peculiar to a liquid transport apparatus that squeezes a tube with plural fingers to transport a liquid.

An aspect of the invention is directed to a liquid transport apparatus including a tube for transporting a liquid, plural fingers that push and block the tube, a cam that pushes the fingers in sequence so as to squeeze the tube to transport the liquid, a first electrode and a second electrode that are provided at the tube located further toward the downstream side than a region pushed by the plural fingers, and a determination unit that determines the presence/absence of a bubble on the basis of the impedance between the first electrode and the second electrode.

Other features of the invention will become clear from the description of the present specification and the accompanying drawings.

BRIEF DESCRIPTION OF THE DRAWINGS

The invention will be described with reference to the accompanying drawings, wherein like numbers reference like elements.

DESCRIPTION OF EXEMPLARY EMBODIMENTS

At least the following matters become evident from the description of the present specification and the accompanying drawings.

A liquid transport apparatus which includes a tube for transporting a liquid, plural fingers that push and block the tube, a cam that pushes the fingers in sequence so as to squeeze the tube to transport the liquid, a first electrode and a second electrode that are provided at the tube located further toward the downstream side than a region pushed by the plural fingers, and a determination unit that determines the presence/absence of a bubble on the basis of the impedance between the first electrode and the second electrode is evident.

According to such a liquid transport apparatus, it is possible to discriminate the presence/absence of bubbles.

It is desirable to perform water-repellent treatment on an inner peripheral surface of the tube. This facilitates detection of bubbles.

When the impedance between the first electrode and the second electrode is measured, it is desirable to apply an alternating voltage to the first electrode and the second electrode so that a bias voltage is not applied between the first electrode and the second electrode. This can keep an electrochemical process from occurring in the liquid.

In the case of priming processing of causing the inside of a flow channel of the liquid transport apparatus to be filled with the liquid, it is desirable to determine that the priming processing is not completed when the determination unit continues determining that a bubble is present. This also enables the determination unit to discriminate the completion of the priming processing.

It is desirable that a third electrode is further provided separately from the first electrode and the second electrode, and the determination unit determines the size of bubbles on the basis of the impedance between the first electrode and the second electrode and the impedance between two separate electrodes. This enables the size of bubbles to be determined.

In a bubble determination method of a liquid transport apparatus including a tube for transporting a liquid, plural fingers that push and block the tube, and a cam that pushes the fingers in sequence so as to squeeze the tube to transport the liquid, the bubble determination method including determining the presence/absence of a bubble on the basis of the impedance between a first electrode and a second electrode that are provided at the tube located further toward the downstream side than a region pushed by the plural fingers becomes evident. This enables the presence/absence of a bubble to be discriminated.

Embodiments

Basic Configuration of Liquid Transport Apparatus

Figure 1:
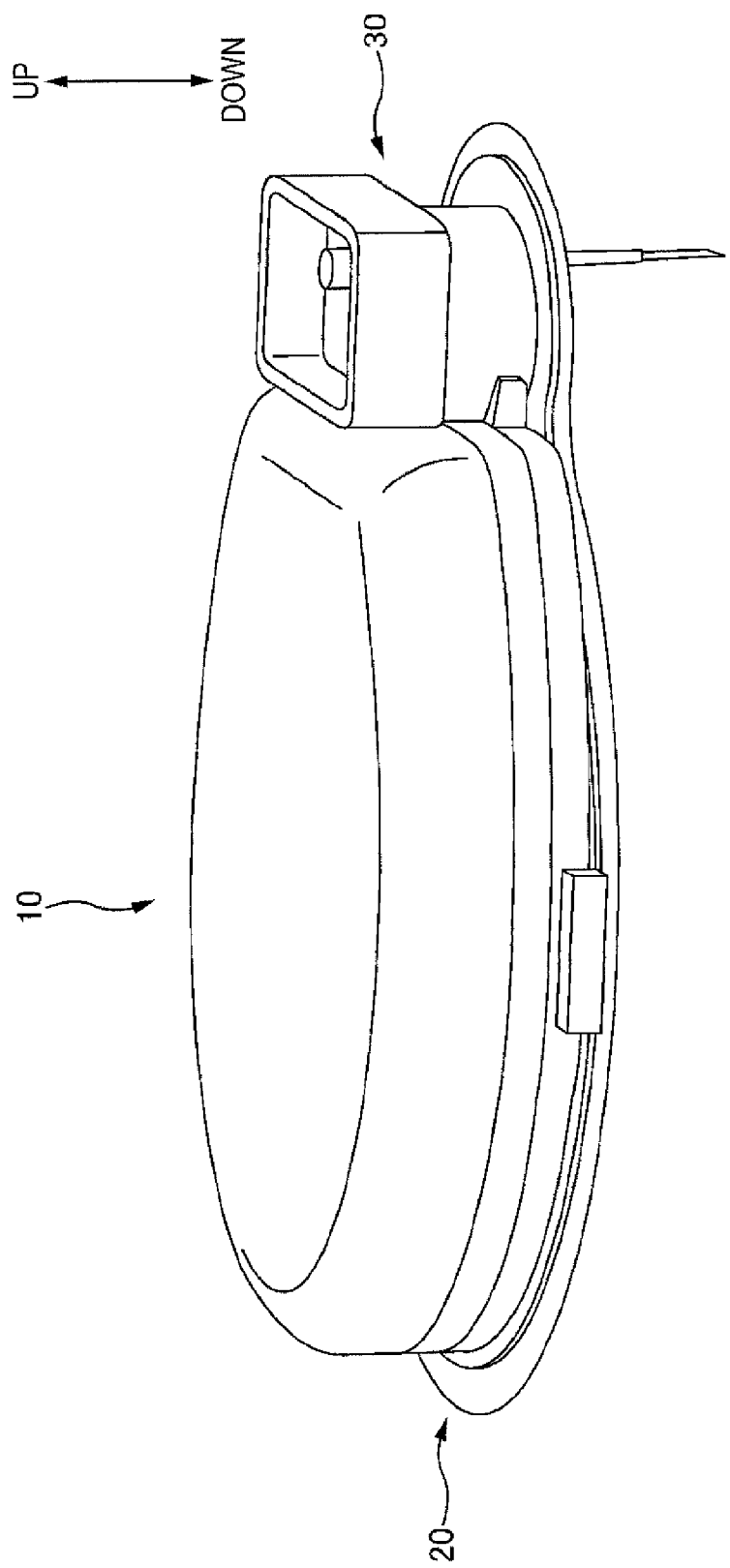
FIG. 1 is an overall perspective view of a liquid transport apparatus.
Figure 2:
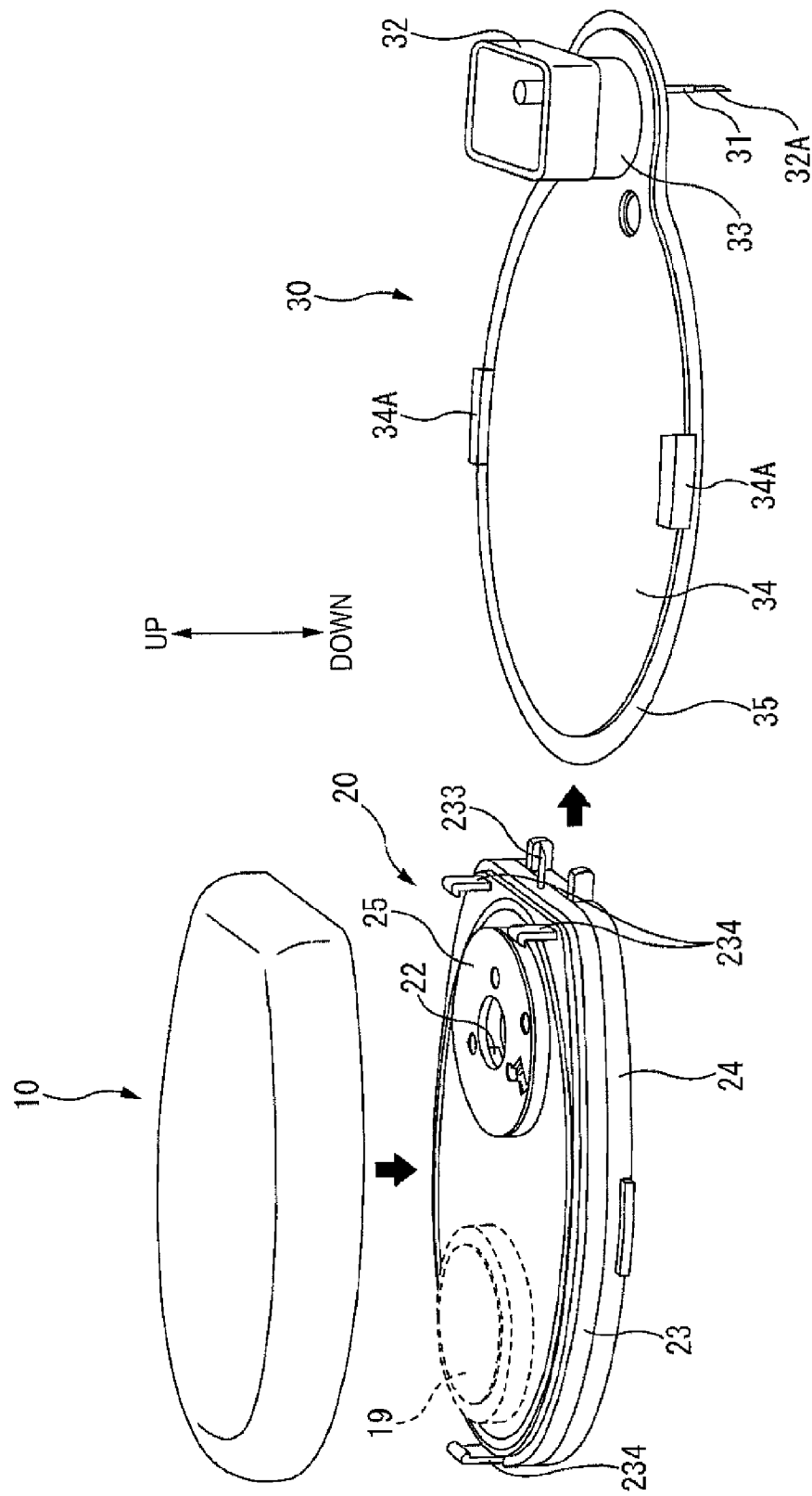
FIG. 2 is an exploded view of the liquid transport apparatus.

FIG. 1 is an overall perspective view of a liquid transport apparatus 1. FIG. 2 is an exploded view of the liquid transport apparatus 1. As shown in the drawings, description may be made with a side (living body side) to which the liquid transport apparatus 1 is adhered being defined as "down", and its opposite side being defined as "up".

The liquid transport apparatus 1 is an apparatus for transporting a liquid. The liquid transport apparatus 1 includes a main body 10, a cartridge 20, and a patch 30. The main body 10, the cartridge 20, and the patch 30 are separable as shown in FIG. 2, but are integrally assembled as shown in FIG. 1 in use. The liquid transport apparatus 1 is favorably used, for example, for adhering the patch 30 to a living body and regularly injecting insulin stored in the cartridge 20. When the liquid (for example, insulin) stored in the cartridge 20 runs out, the cartridge 20 is replaced, but the main body 10 and the patch 30 continue being used. However, the patch 30 is also replaced at low frequency.

Figure 3:
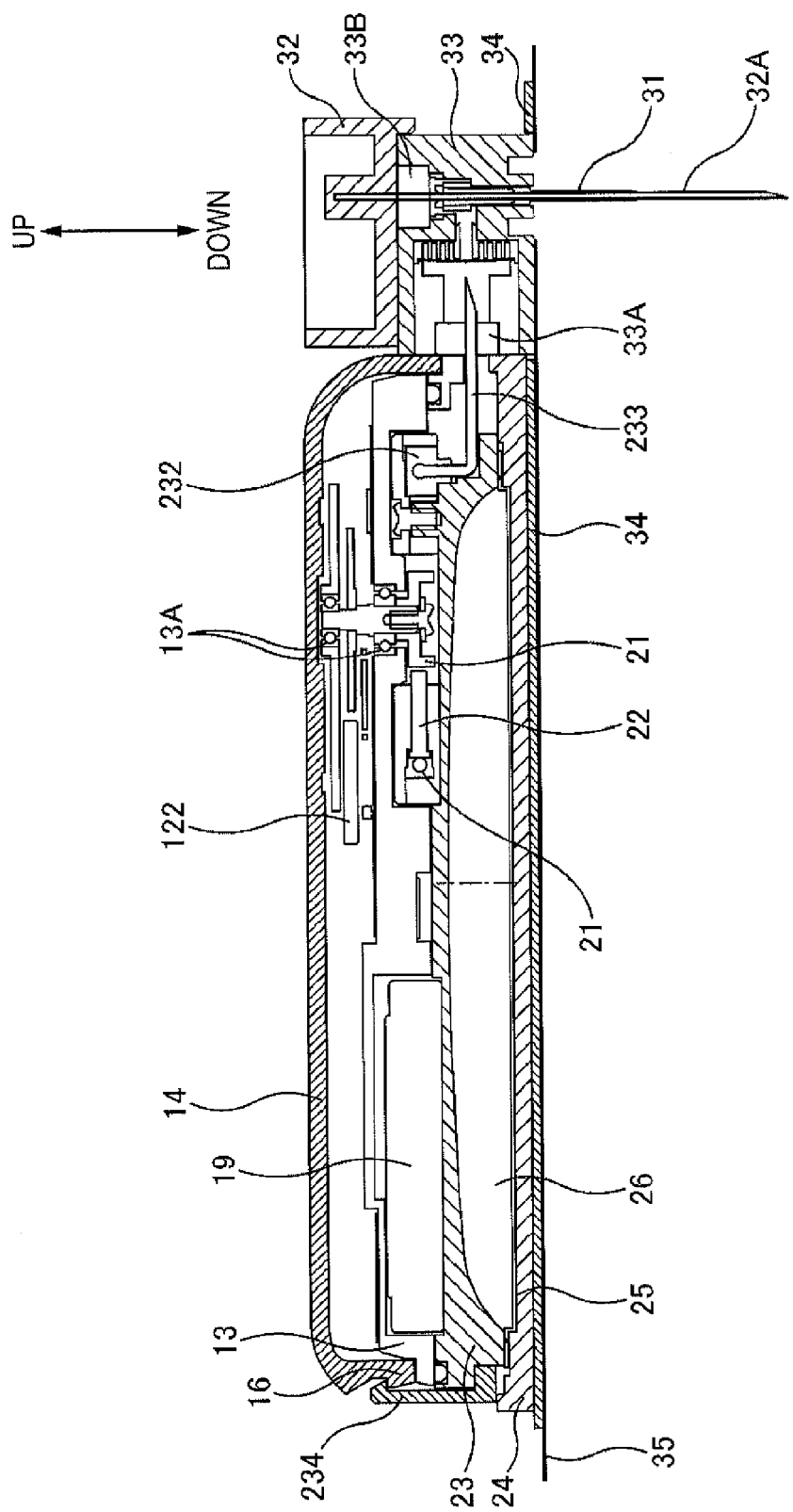
FIG. 3 is a cross-sectional view of the liquid transport apparatus.
Figure 4:
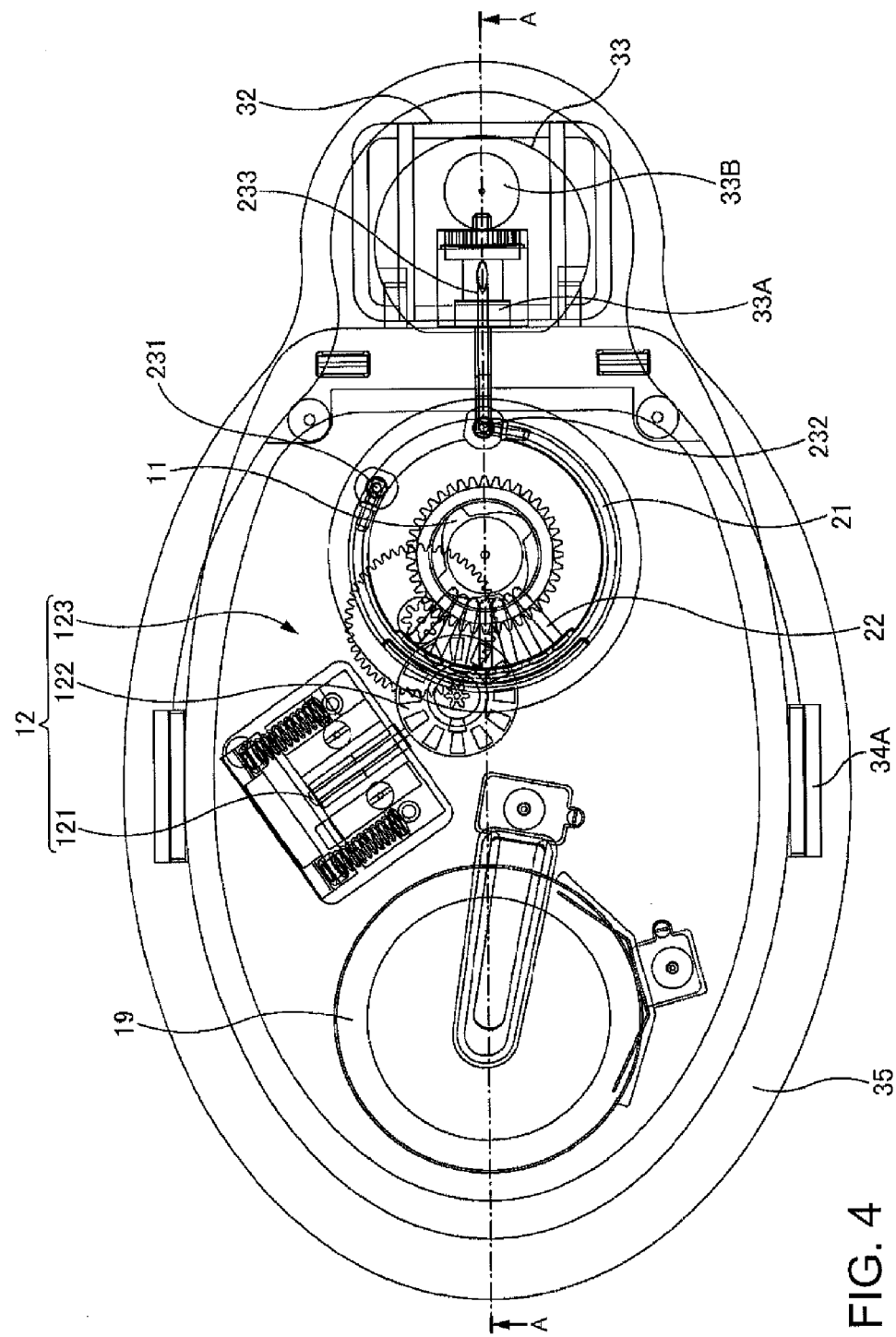
FIG. 4 is a projected top view of the inside of the liquid transport apparatus.
Figure 5:
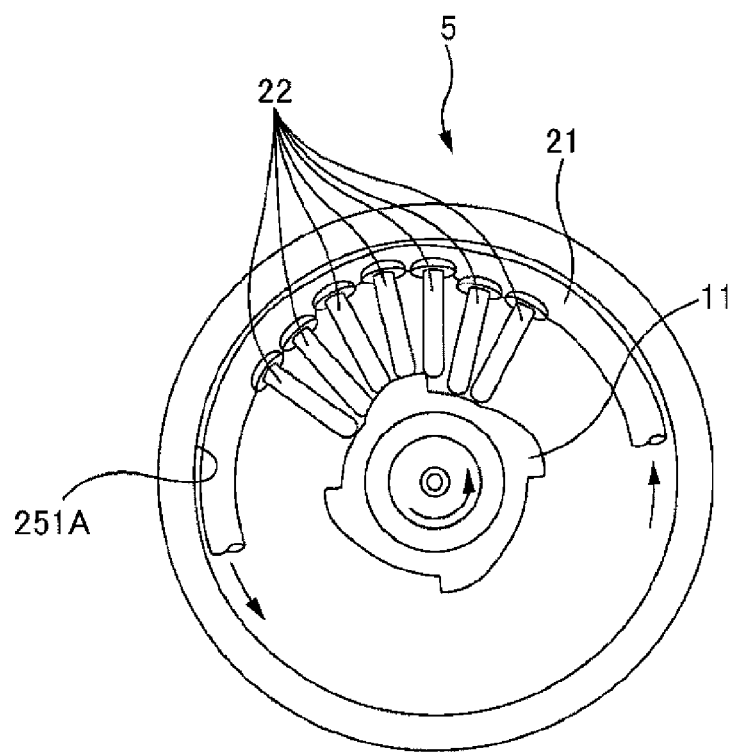
FIG. 5 is a schematic explanatory view of a pump unit.

FIG. 3 is a cross-sectional view of the liquid transport apparatus 1. FIG. 4 is a projected top view of the inside of the liquid transport apparatus 1. The configuration of a pump unit 5 is also shown in FIG. 4. FIG. 5 is a schematic explanatory view of the pump unit 5.

The pump unit 5 has a function as a pump for transporting the liquid stored in the cartridge 20, and includes a tube 21, plural fingers 22, a cam 11, and a drive mechanism 12.

The tube 21 is a tube for transporting the liquid. An upstream side (upstream side when being based on a transport direction of the liquid) of the tube 21 communicates with a liquid storage portion 26 of the cartridge 20. The tube 21 has elasticity to such a degree that the tube is blocked when being pushed by the fingers 22 and is returned to its original state if the force from the fingers 22 is released. The tube 21 is arranged partially in the shape of a circular arc shape along an inner surface of a tube guide wall 251A of the cartridge 20. The circular-arc-shaped portion of the tube 21 is arranged between the inner surface of the tube guide wall 251A and the plural fingers 22. The center of the circular arc of the tube 21 coincides with the rotation center of the cam 11.

The fingers 22 are members for blocking the tube 21. The fingers 22 receive a force from the cam 11 and operate in a following manner. The fingers 22 have a rod-shaped shaft portion and a collar-shaped pressing portion, and are formed in a T-shape. The rod-shaped shaft portion comes into contact with the cam 11, and the collar-shaped pressing portion comes into contact with the tube 21. The fingers 22 are supported so as to be movable along the axial direction.

The plural fingers 22 are arranged at equal intervals radially from the rotation center of the cam 11. The plural fingers 22 are arranged between the cam 11 and the tube 21. Here, seven fingers 22 are provided. In the following description, the plural fingers may be referred to as a first finger 22A, a second finger 22B, . . . , and a seventh finger 22G in sequence from the upstream side in the transport direction of the liquid.

The cam 11 has projection portions in four places of an outer periphery thereof. The plural fingers 22 are arranged at the outer periphery of the cam 11, and the tube 21 is arranged outside the fingers 22. The tube 21 is blocked by the fingers 22 being pushed by the projection portions of the cam 11. If the fingers 22 come off the projection portions, the tube 21 returns to its original shape by the elastic force of the tube 21. If the cam 11 rotates, the seven fingers 22 are pushed in sequence from the projection portions, and the tube 21 is blocked sequentially from the upstream side in the transport direction. This causes the tube 21 to perform a peristaltic motion so as to squeeze and transport the liquid. In order to prevent flowback of the liquid, the projection portions of the cam 11 are formed so that at least one or preferably two fingers 22 block the tube 21.

The drive mechanism 12 is a mechanism for rotating the cam 11. The drive mechanism 12 has a piezoelectric motor 121, a rotor 122, and a reduced speed transmission mechanism 123 (refer to FIG. 4).

The piezoelectric motor 121 is a motor for rotating the rotor 122 using vibration of piezoelectric devices. The piezoelectric motor 121 applies a driving signal to the piezoelectric devices bonded on both faces of a rectangular vibrating body, to thereby vibrate the vibrating body. An end portion of the vibrating body comes into contact with the rotor 122, and if the vibrating body vibrates, the end portion vibrates while drawing predetermined tracks, such as an elliptical track or an 8-shaped track. When the end portion of the vibrating body comes into contact with the rotor 122 in a portion of a vibrating track, the rotor 122 is rotationally driven. The piezoelectric motor 121 is biased toward the rotor 122 with a pair of springs so that the end portion of the vibrating body comes into contact with the rotor 122.

The rotor 122 is a driven body rotated by the piezoelectric motor 121. The rotor 122 is formed with a rotor pinion that constitutes a portion of the reduced speed transmission mechanism 123.

The reduced speed transmission mechanism 123 is a mechanism that transmits the rotation of the rotor 122 to the cam 11 in a predetermined reduction ratio. The reduced speed transmission mechanism 123 is constituted by the rotor pinion, a transmission wheel, and a cam gear. The rotor pinion is a pinion integrally attached to the rotor 122. The transmission wheel has a main gear that meshes with the rotor pinion and a pinion that meshes with the cam gear and has a function to transmit the rotative force of the rotor 122 to the cam 11. The cam gear is integrally attached to the cam 11 and is rotatably supported together with the cam 11.

Among the tube 21, the plural fingers 22, the cam 11, and the drive mechanism 12 that constitute the pump unit 5, the cam 11 and the drive mechanism 12 are provided at the main body 10, and the tube 21 and the plural fingers 22 are provided at the cartridge 20. Hereinafter, the configuration of the main body 10, the cartridge 20, and the patch 30 will be described.

Main Body 10

Figure 6:
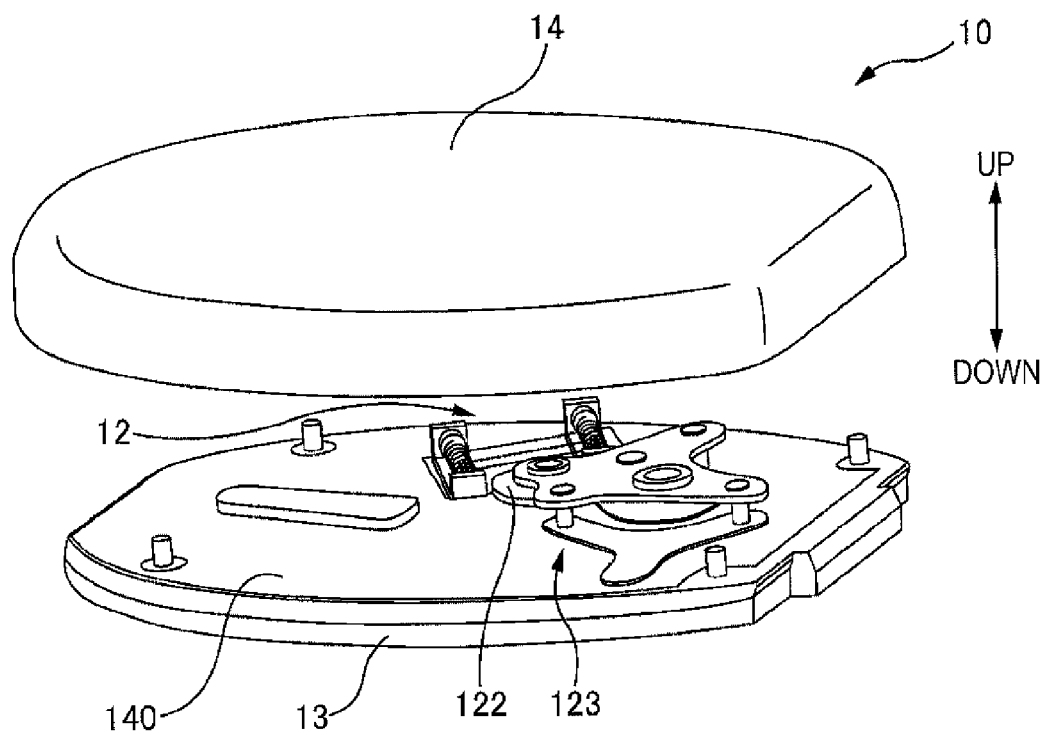
FIG. 6 is an exploded perspective view showing an internal configuration of a main body.
Figure 7:
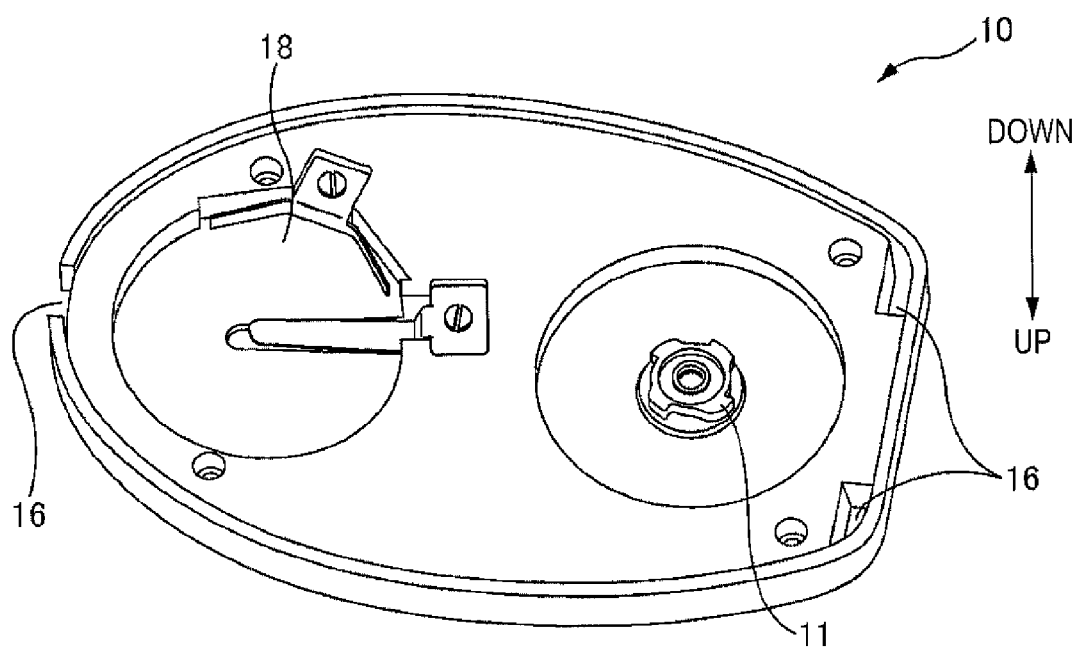
FIG. 7 is a perspective view of a rear surface of the main body.

FIG. 6 is an exploded perspective view showing an internal configuration of the main body 10. FIG. 7 is a perspective view of a rear surface of the main body 10. Hereinafter, the configuration of the main body 10 will be described referring to FIGS. 1 to 4 together with these drawings.

The main body 10 has a main body base 13 and a main body case 14. The aforementioned drive mechanism 12 and a control board 15 (control unit) that performs control of the piezoelectric motor 121 or the like are provided on the main body base 13. The drive mechanism 12 (the piezoelectric motor 121, the rotor 122, the reduced speed transmission mechanism 123) and the control board 15 on the main body base 13 are covered with and protected by the main body case 14.

The main body base 13 is provided with a bearing 13A. A rotating shaft of the cam 11 penetrates the main body base 13, and the bearing 13A rotatably supports the rotating shaft of the cam 11 with respect to the main body base 13. The cam 11 is integral with the cam gear that constitutes the reduced speed transmission mechanism 123, and the cam gear is covered with the main body case 14 and is arranged inside the main body 10, and the cam 11 is exposed from the main body 10. If the main body 10 and the cartridge 20 are combined together, the cam 11 exposed from the main body 10 meshes with end portions of the fingers 22 of the cartridge 20.

The main body 10 is provided with a hook catch 16. A fixing hook 234 of the cartridge 20 is caught in the hook catch 16 to fix the main body 10 to the cartridge 20.

Additionally, the main body 10 has a battery housing portion 18. A battery 19 housed in the battery housing portion 18 serves as an electric power source of the liquid transport apparatus 1.

Cartridge 20

Figure 8:
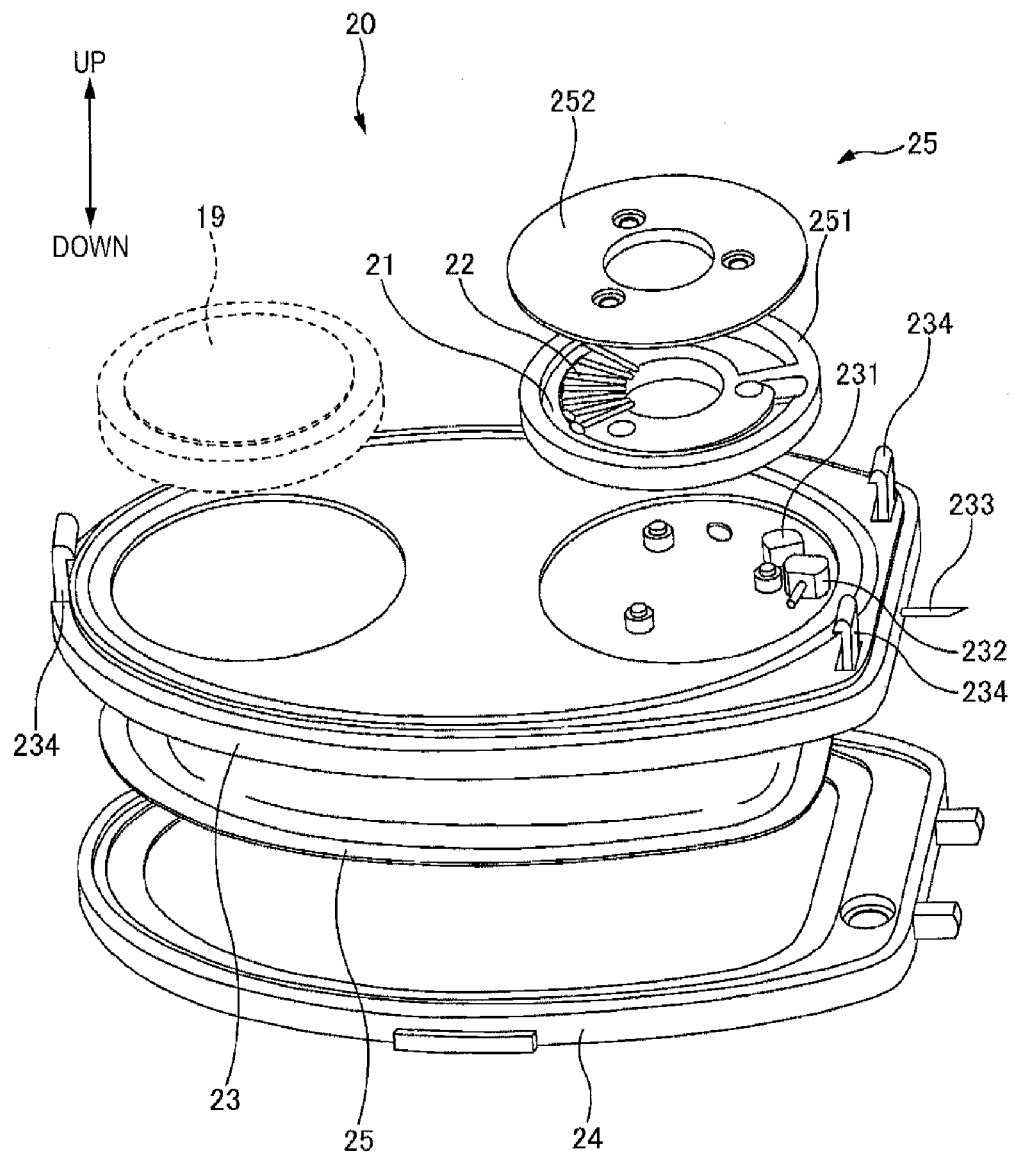
FIG. 8 is an exploded perspective view showing an internal configuration of a cartridge.
Figure 9:
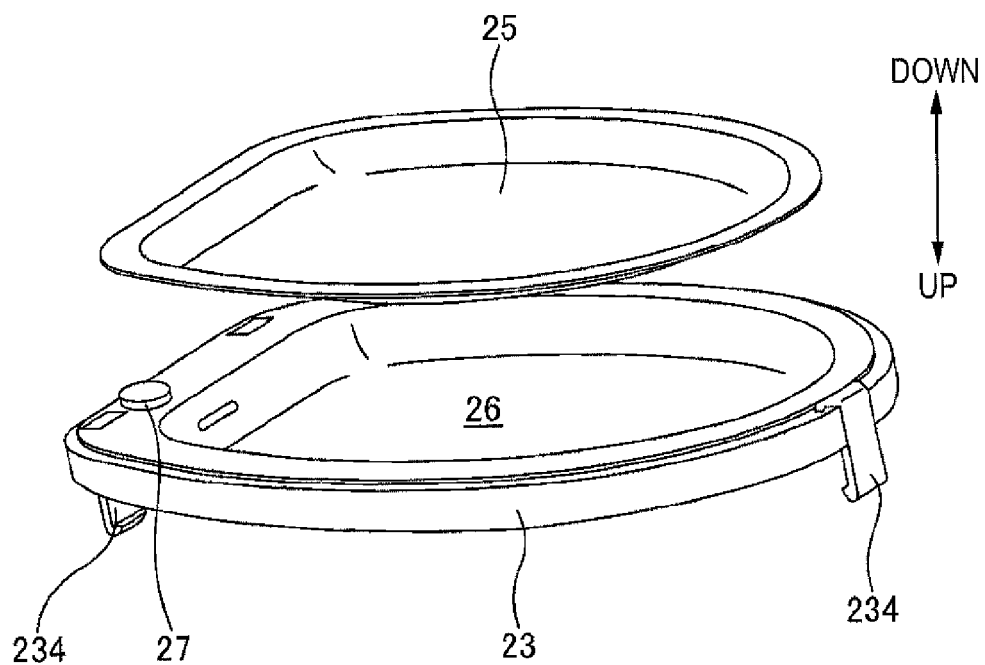
FIG. 9 is an exploded perspective view of a rear surface of a base of the cartridge.

FIG. 8 is an exploded perspective view showing an internal configuration of the cartridge 20. FIG. 9 is an exploded perspective view of a rear surface of a base of the cartridge 20. Hereinafter, the configuration of the cartridge 20 will be described referring to FIGS. 1 to 5 together with these drawings.

The cartridge 20 has a cartridge base 23 and a base receptacle 24.

A tube unit 25 is provided on the upper side of the cartridge base 23. The tube unit 25 has the afore-mentioned tube 21 and plural fingers 22, a unit base 251, and a unit cover 252. The unit base 251 is formed with the tube guide wall 251A, and the tube 21 is arranged in the shape of a circular arc inside the unit base 251. Additionally, the unit base 251 supports the fingers 22 so as to be movable in the axial direction. The tube 21 and the fingers 22 within the unit base 251 are covered with the unit cover 252.

The tube unit 25 is formed in a flat cylindrical shape, and the cam 11 exposed from the main body 10 is inserted into a central cavity of the tube unit 25. This allows the fingers 22 on the cartridge 20 side to mesh with the cam 11 on the main body 10 side.

The cartridge base 23 is provided with a supply-side joint 231 and a discharge-side joint 232. End portions of the tube 21 within the tube unit 25 are connected to the supply-side joint 231 and the discharge-side joint 232, respectively. If the plural fingers 22 squeeze the tube 21 in sequence, the liquid is supplied from the supply-side joint 231 to the tube 21 and the liquid is discharged from the discharge-side joint 232. A connecting needle 233 communicates with the discharge-side joint 232, and the liquid discharged from the discharge-side joint 232 is supplied to the patch 30 side via the connecting needle 233.

The cartridge base 23 is formed with the fixing hook 234. The fixing hook 234 is caught in the hook catch 16 of the main body 10 to fix the main body 10 to the cartridge 20.

A reservoir film 25 is pinched between the cartridge base 23 and the base receptacle 24. The periphery of the reservoir film 25 is tightly bonded to a bottom surface of the cartridge base 23. The storage portion 26 is formed between the cartridge base 23 and the reservoir film 25, and the liquid (for example, insulin) is stored in the storage portion 26. The storage portion 26 communicates with the supply-side joint 231, and the liquid stored in the storage portion 26 is supplied to the tube 21 via the supply-side joint 231.

The storage portion 26 is configured on the lower side of the cartridge base 23 as described above. Since the tube 21 and the fingers 22 that constitute the pump unit 5 are arranged on the upper side of the cartridge base 23, the pump unit 5 and the storage portion 26 are arranged vertically. This achieves miniaturization of the liquid transport apparatus 1. Additionally, the storage portion 26 is arranged further toward the living body side than the pump unit 5. This easily keeps the liquid stored in the storage portion 26 warm at the body temperature of a living body and suppresses the difference between the temperature of the liquid and the body temperature of the living body.

If the liquid stored in the storage portion 26 runs out, the cartridge 20 is removed from the liquid transport apparatus 1 and replaced with a new cartridge 20. However, it is possible to inject the liquid from the outside via a cartridge septum 27 into the storage portion 26 using an injection needle. In addition, the cartridge septum 27 is made of material (for example, rubber, silicon, or the like) that closes a hole if the injection needle is extracted.

Patch 30

Figure 10:
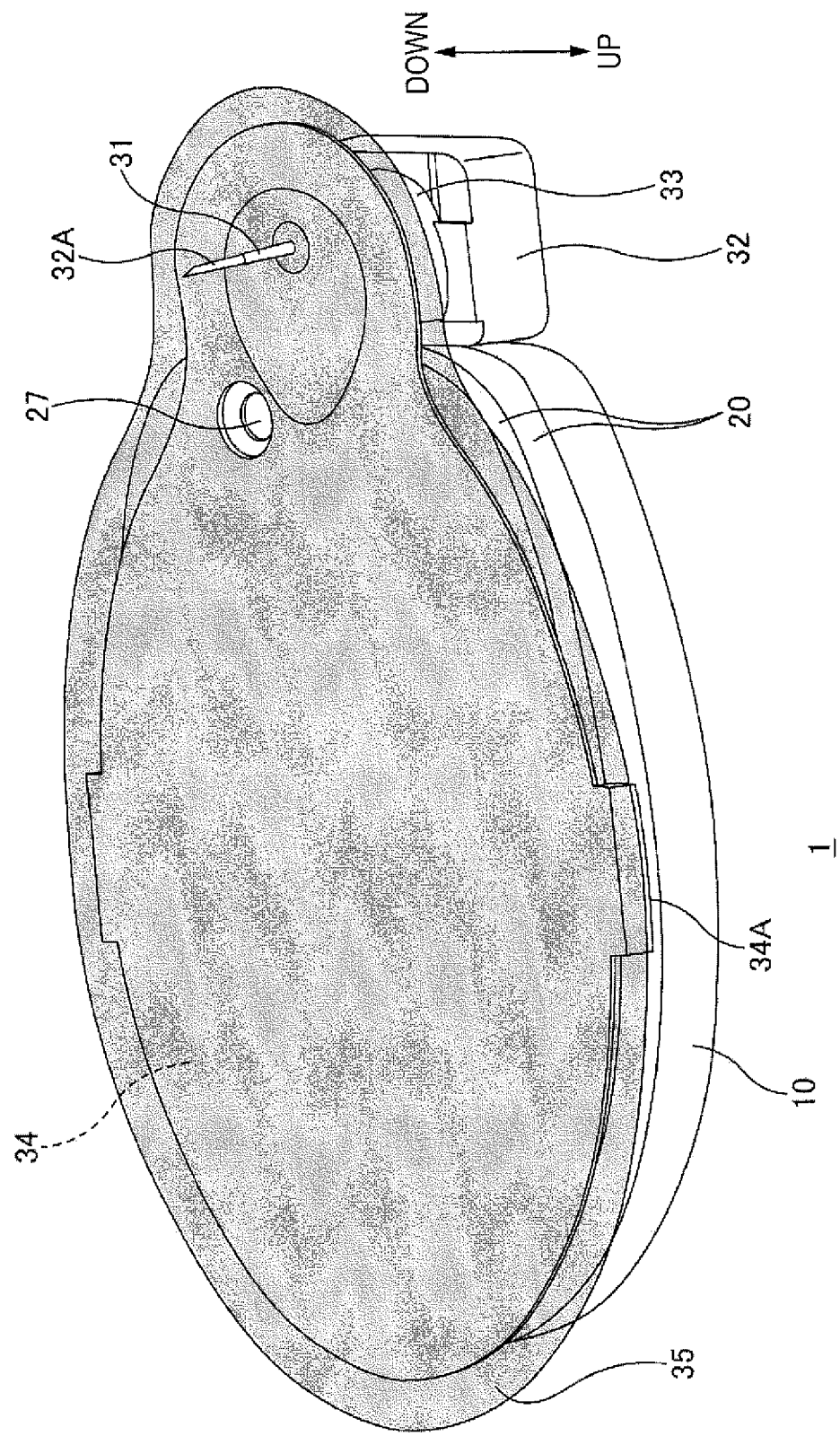
FIG. 10 is a perspective view when the liquid transport apparatus is viewed from a bottom surface side of a patch.

FIG. 10 is a perspective view when the liquid transport apparatus 1 is viewed from the bottom surface side of the patch 30. Hereinafter, the configuration of the patch 30 will be described also referring to FIGS. 1 to 5.

The patch 30 has a soft needle 31, an introduction needle folder 32, a port base 33, a patch base 34, and an adhesion pad 35.

The soft needle 31, which is a tube for injecting the liquid into the living body, has a function of a catheter. The soft needle 31 is made of, for example, flexible material, such as fluororesin. One end of the soft needle 31 is fixed to the port base 33.

The introduction needle folder 32 is a member that holds an introduction needle 32A. One end of the introduction needle 32A is fixed to the introduction needle folder 32. The introduction needle 32A is a metal needle for inserting the flexible soft needle 31 into the living body. The introduction needle 32A is an elongated hollow tubular needle and has a lateral hole (not shown). If the liquid is supplied from the lateral hole of the introduction needle 32A, the liquid is discharged from the tip of the introduction needle 32A. This enables the priming processing of causing the inside of the flow channel of the liquid transport apparatus 1 to be filled with the liquid before the soft needle 31 punctures the living body.

In the state before use, the introduction needle folder 32 is attached to the port base 33, and the introduction needle 32A is inserted through the soft needle 31 and a needle point thereof is exposed from the lower side of the soft needle 31. When the patch 30 is pasted on the living body, after the soft needle 31 has punctured the living body together with the introduction needle 32A, the introduction needle folder 32 is pulled out (extracted) from the port base 33 together with the introduction needle 32A. Since the hard introduction needle 32A does not continue to be indwelled in the living body, a burden on the living body is small. In addition, although the soft needle 31 continues being indwelled in the living body, since the soft needle 31 is soft, the load to the living body is small.

The port base 33 is a member that supplies the liquid, which is supplied from the connecting needle 233 of the cartridge 20, to the soft needle 31. The port base 33 has a septum 33A for a connecting needle and a septum 33B for an introduction needle. The septum 33A for a connecting needle and the septum 33B for an introduction needle are made of material (for example, rubber, silicon, or the like) that closes a hole if the needle is extracted. The connecting needle 233 of the cartridge 20 is inserted through the septum 33A for a connecting needle, and the liquid is supplied from the cartridge 20 side to the patch 30 side through the septum 33A for a connecting needle via the connecting needle 233. Even if the connecting needle 233 of the cartridge 20 is extracted from the patch 30 for replacement of the cartridge 20, a hole of the septum 33A for a connecting needle formed by the connecting needle 233 is spontaneously closed. The introduction needle 32A is inserted through the septum 33B for an introduction needle, and if the introduction needle 32A is pulled out, a hole of the septum 33B for an introduction needle formed by the introduction needle 32A is spontaneously closed. The septum 33A for a connecting needle and the septum 33B for an introduction needle prevent the liquid within the patch 30 from leaking to the outside as well as prevent bodily fluids of the living body from flowing back to the patch 30 side. In addition, a region (regions other than the septum for an introduction needle) where the introduction needle 32A is present within the port base 33 serves as a flow channel for the liquid after the extraction of the introduction needle 32A.

The patch base 34 is a plate-shaped member fixed to the port base 33. The patch base 34 has a fixing portion 34A for fixing the base receptacle 24. The adhesion pad 35 is attached to a bottom surface of the patch base 34. The adhesion pad 35 is an adhesive pad for adhering the patch 30 to the living body or the like.

In the above liquid transport apparatus 1, the pump unit 5 and the storage portion 26 are arranged vertically, and the downsizing of the liquid transport apparatus 1 is achieved. This enables the adhesion pad 35 to be downsized.

Basic Using Method

Figure 11:
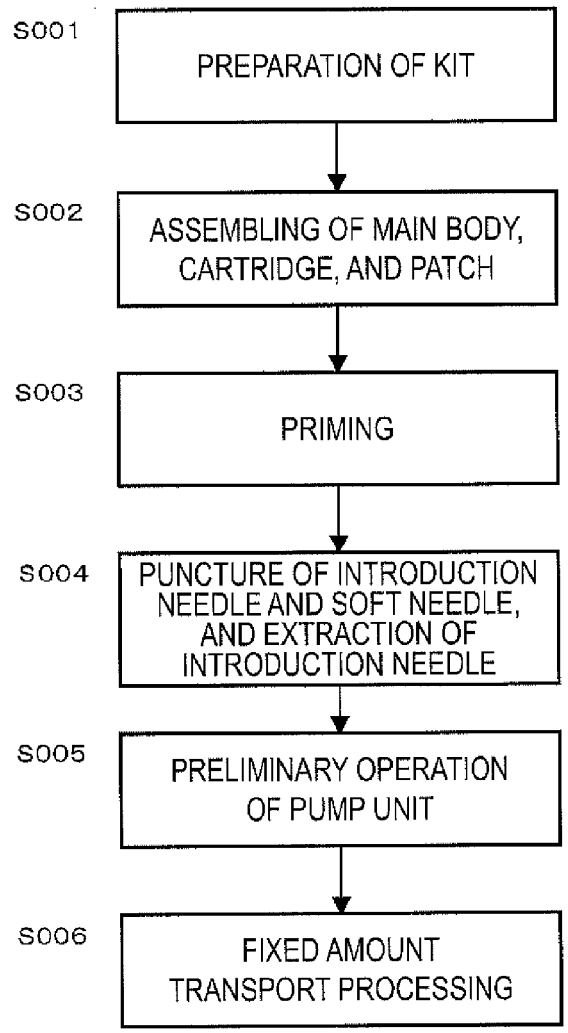
FIG. 11 is a flow diagram showing a method of using the liquid transport apparatus.

FIG. 11 is a flow diagram showing a method of using the liquid transport apparatus 1.

First, a user prepares a kit that is the liquid transport apparatus 1 (S001). The main body 10, the cartridge 20, and the patch 30 for constituting the liquid transport apparatus 1 are included in the kit. As shown in FIG. 2, the user assembles the main body 10, the cartridge 20, and the patch 30 to assemble the liquid transport apparatus 1 (S002). The user assembles the main body 10 and the cartridge 20 to thereby cause the cam 11 on the main body 10 side to mesh with the fingers 22 on the cartridge 20 side. Additionally, the user inserts the connecting needle 233 of the cartridge 20 into the septum 33A for a connecting needle of the patch 30 and brings the connecting needles into a state where the liquid can be supplied from the cartridge 20 side to the patch 30 side.

Figure 12:
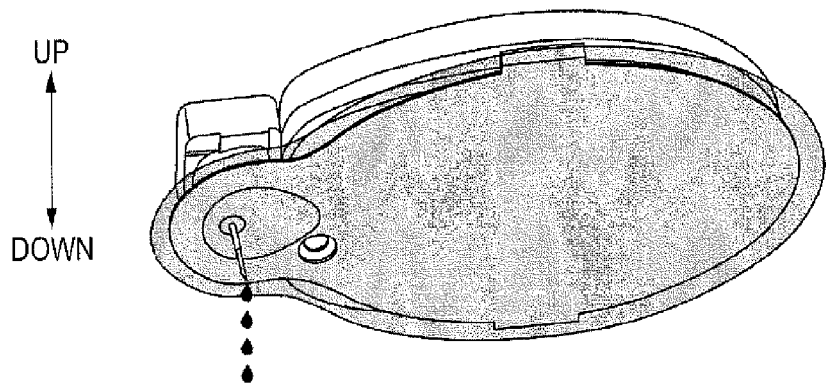
FIG. 12 is an explanatory view of priming processing.

Next, the user performs the priming processing (S003). FIG. 12 is an explanatory view of the priming processing. The priming processing is the processing of driving the pump unit 5 of the liquid transport apparatus 1 to cause the inside of the flow channel of the liquid transport apparatus 1 to be filled with the liquid. The gas within the flow channel of the liquid transport apparatus 1 is discharged from the introduction needle 32A by this priming processing. Additionally, the tube 21 in an empty state is filled with the liquid by this priming processing. The user drives the pump unit 5 of the liquid transport apparatus 1 until the liquid is discharged from the tip of the introduction needle 32A.

After the priming processing, the user perpendicularly punctures the living body with the introduction needle 32A and the soft needle 31, then pulls out the introduction needle folder 32 from the port base 33, and extracts the introduction needle 32A from the soft needle 31 (S004). Since there is the septum 33B for an introduction needle, even if the introduction needle 32A is extracted, the hole of the septum 33B for an introduction needle formed by the introduction needle 32A is spontaneously closed. At this time, the user may peel a protection sheet of the adhesion pad 35 of the patch 30 to paste the adhesion pad 35 on the skin of the living body to adhere the liquid transport apparatus 1 to the living body.

Next, the user preliminarily operates the pump unit 5 so as to transport the liquid equivalent to the volume of the region (regions other than the septum for an introduction needle) where the introduction needle 32A is present (S005). This enables a space where the introduction needle 32A is present to be filled with the liquid.

Then, the user makes the liquid transport apparatus perform fixed amount transport processing (normal processing) (S006). At this time, the liquid transport apparatus 1 drives the piezoelectric motor 121 of the drive mechanism 12 to rotate the cam 11, pushes the seven fingers 22 in sequence using the projection portions of the cam 11 to make the tube 21 blocked sequentially from the upstream side in the transport direction, and causes the tube 21 to perform a peristaltic motion to transport the liquid. In the fixed amount transport processing, the rotational amount of the cam 11 is controlled so that a predetermined amount of liquid is transported in a predetermined time.

Generation of Bubble

As will be described below, when the tube 21 is squeezed by the fingers 22 to transport the liquid, bubbles are generated with the operation of the fingers 22. Particularly, large bubbles are generated when the plural fingers 22 are used.

FIGS. 13A to 13D are explanatory views of generation of bubbles. Although the tube 21 is originally arranged in the shape of a circular arc, here, the tube 21 is arranged in a linear fashion for convenience.

As the cam 11 rotates, shift is made from a state (FIG. 13A) where the seventh finger 22G has blocked the tube 21 to a state (FIG. 13B) where a pressed state obtained by the seventh finger 22G is released. At this time, the liquid of the tube 21 near the seventh finger 22G is apt to have a negative pressure, and as a result, gas dissolved in the liquid may become minute bubbles. In this stage, the minute bubbles adhere to the inner wall of the tube 21 and are not transported together with the liquid. Additionally, the minute bubbles do not have such a size that the tube is blocked.

Minute bubbles are similarly generated within the tube 21 even in other fingers 22 as well as in the seventh finger 22G. Then, if the rotation of the cam 11 is continued and the blocking and opening of the tube 21 by the fingers 22 are repeated, as shown in FIG. 13C, minute bubbles develop.

Figure 13A:
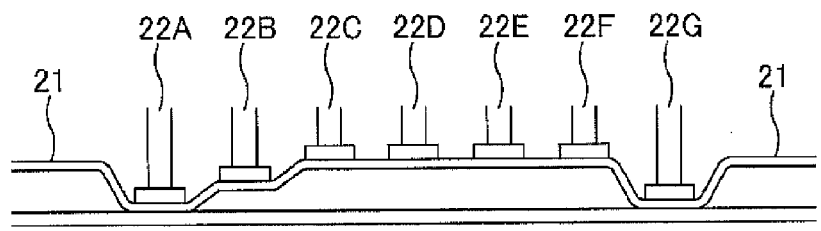
FIGS. 13A to 13D are explanatory views of generation of bubbles.
Figure 13B:
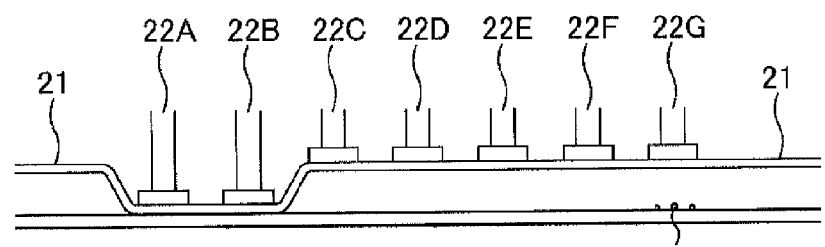
Figure 13C:
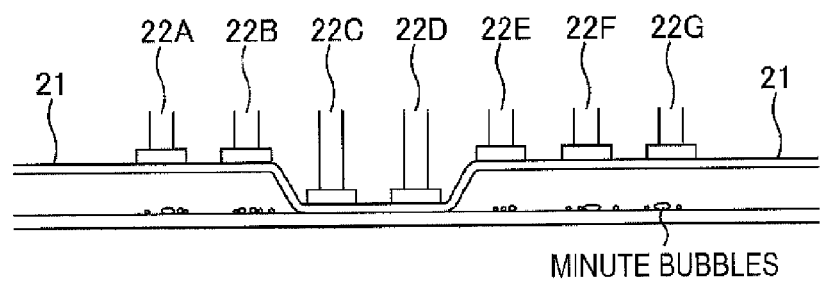
Figure 13D:
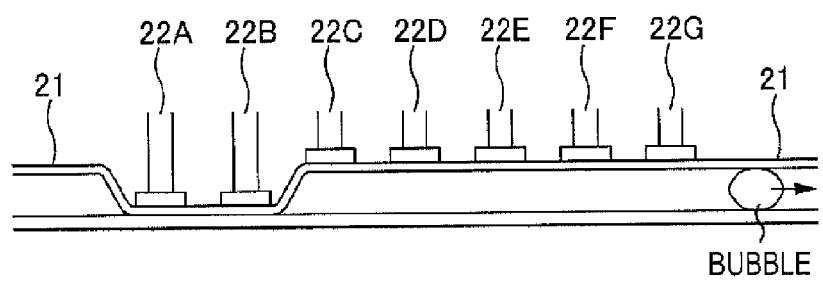

If the minute bubbles develop as shown in FIG. 13C, relatively large minute bubbles are separated from the inner wall of the tube 21 and are easily transported together with the liquid. The minute bubbles separated from the inner wall on the upstream side of the tube 21 involve and integrate minute bubbles on the downstream side, and as shown in FIG. 13D, an integrated bubble is transported in the transport direction. The integrated bubble has such a size that the tube 21 is blocked.

When the tube is squeezed by the plural fingers 22 to transport the liquid in this way, since minute bubbles generated in plural places with the operation of the respective fingers 22 are integrated, a bubble develops with such a size that the tube 21 is blocked. The integrated bubble moves to the downstream side inside the tube 21.

In addition, if gas is dissolved in the liquid, bubbles may be generated in every place. For example, if temperature changes, bubbles may be generated in the liquid in the storage portion 26 or the liquid in the tube 21. Additionally, the pressure fluctuation of the liquid accompanying tube diameter changes in the joints (the supply-side joint 231 and the discharge-side joint 232) may become a cause to generate bubbles. However, the bubbles generated by these causes have a size equivalent to the above minute bubbles, and these bubbles independently cannot easily have such a size that the tube 21 is blocked. In contrast, when the tube 21 is squeezed by the plural fingers 22 to transport the liquid, bubbles are apt to have such a size that the tube 21 is blocked.

Bubble Determination

Figure 14:
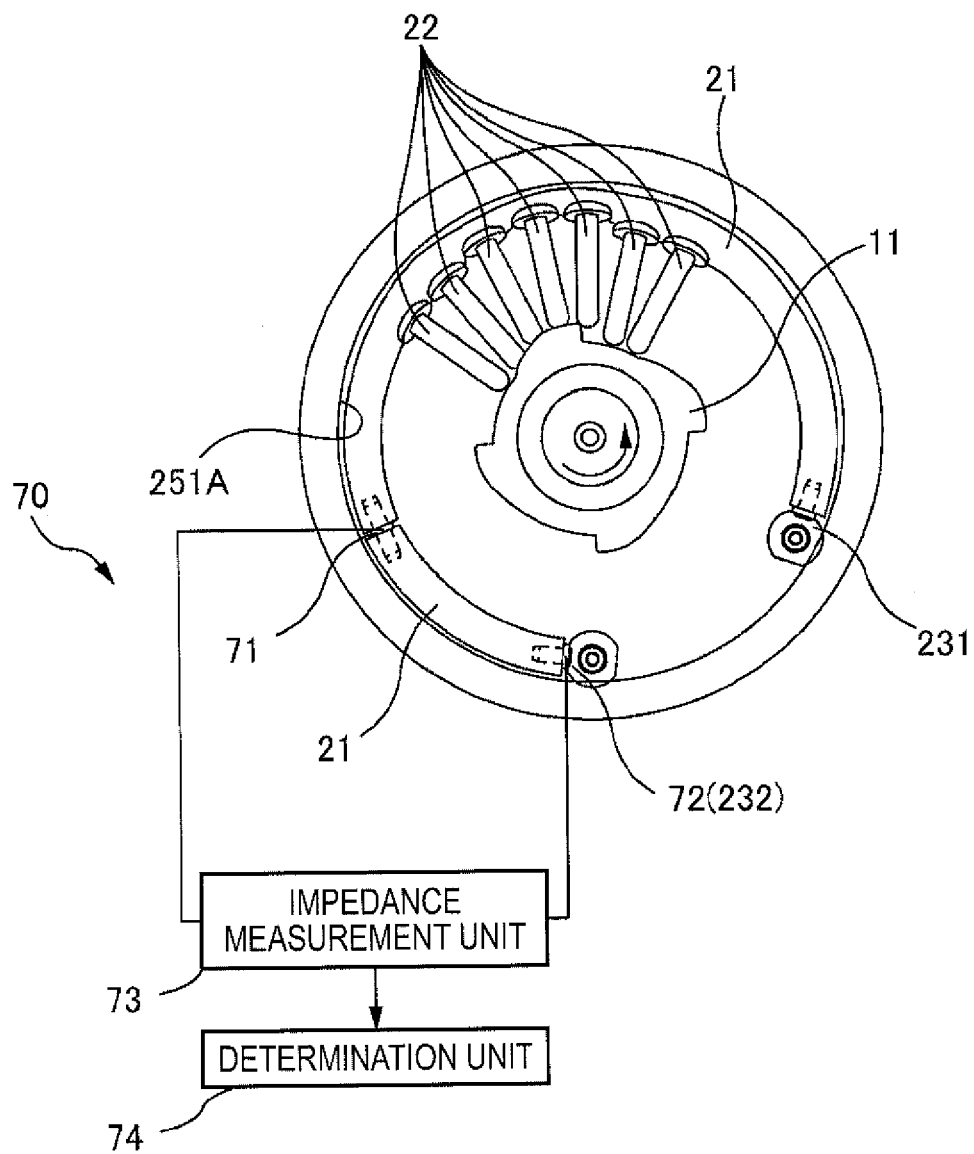
FIG. 14 is an explanatory view of a monitoring device that monitors bubbles within a tube of the present embodiment.

FIG. 14 is an explanatory view of a monitoring device 70 that monitors bubbles within the tube 21 of the present embodiment.

The monitoring device 70 has a first electrode 71, a second electrode 72, an impedance measuring unit 73, and a bubble determination unit 74. The first electrode 71 is located further the upstream side than the second electrode 72. The impedance measuring unit 73 and the bubble determination unit 74 are provided on the aforementioned control board 15.

The first electrode 71 and the second electrode 72 are provided at the tube 21 located further toward the downstream side than a region pushed by the fingers 22. The reason why the first electrode 71 and the second electrode 72 are provided at such positions is because bubbles are generated in the region where the fingers 22 push the tube 21, the bubbles move to the downstream side from there (refer to FIG. 13D), and the bubbles are detected.

The first electrode 71 and the second electrode 72 are tubular, and constitute a flow channel that comes into contact with the liquid at an inner peripheral surface thereof and allows the liquid to be transported therethrough. In the present embodiment, the first electrode 71 and the second electrode 72 come into direct contact with the liquid. Therefore, compared to a case (when the electrodes are provided outside the tube and the electrodes do not come into direct contact with the liquid) where the electrodes and the liquid are capacitively coupled to each other, an error when the impedance is measured can be reduced, and the accuracy of the measurement improves.

Specifically, the first electrode 71 and the second electrode 72 are constituted by conductive metal joints. The first electrode 71 is a straight tubular joint that couples the tubes 21 on the upstream side and the downstream side to each other. The second electrode 72 is an L-shaped joint for allowing the tube 21 and the connecting needle 233 to communicate with each other and serves also as the discharge-side joint 232 here.

The impedance measuring unit 73 measures the impedance between the first electrode 71 and the second electrode 72.

Figure 15:
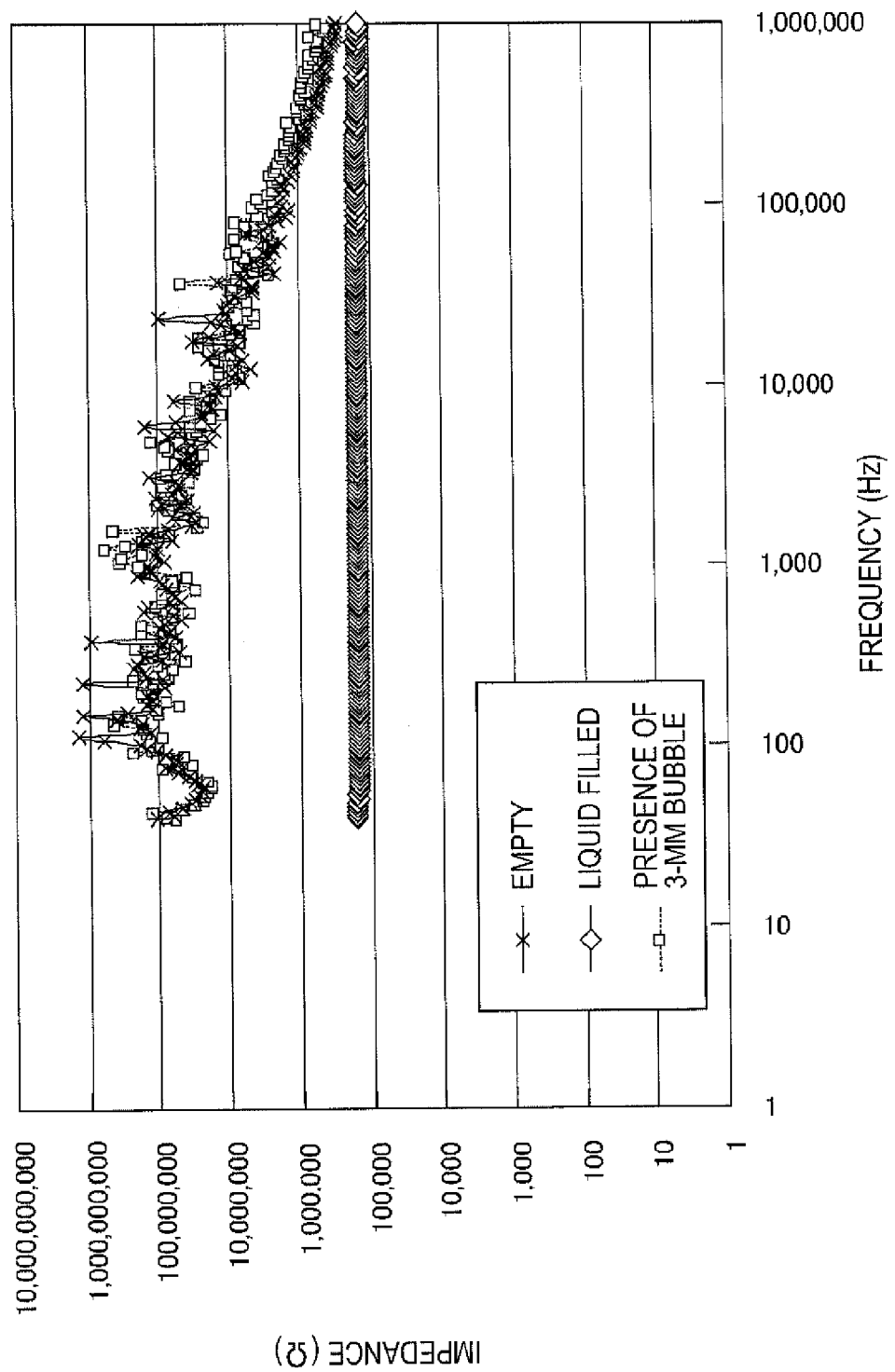
FIG. 15 shows a graph of experimental results of measurement of impedance by an impedance measuring unit.

FIG. 15 shows a graph of experimental results of measurement of the impedance by the impedance measuring unit 73. The horizontal axis of the graph is the frequency [Hz] of an alternating voltage of the impedance measuring unit 73, and the vertical axis of the graph is the impedance [Ω] measured by the impedance measuring unit 73. In addition, although the frequency of the alternating voltage of the impedance measuring unit 73 is within a range of 1 kHz to 10 kHz in practice, measurement is performed in a broad band in the experiment.

As for the tube 21 used for the experiment, an internal diameter D is 0.57 [mm] and an area S is 0.00255 [cm] (however, in the experiment, the length between the first electrode 71 and the second electrode 72 is made longer than in practice). Additionally, the liquid used for the experiment is 0.9% physiological salt solution, the conductivity is 0.016 [S/cm] and the specific resistance is 62.5 [Ωcm], under the condition of 25° C. In the experiment, measurement of the impedance between the first electrode 71 and the second electrode 72 is performed regarding three ways of a state where the tube 21 is empty, a state where the tube 21 is filled with the liquid, and a state where there is an 3-mm bubble while the tube 21 is filled with the liquid. In addition, if a bubble having a length of 3 mm is in the tube 21, the tube 21 is blocked by the bubble.

As shown on the graph, the impedance is equal to or higher than 10 MΩ (a frequency range of 1 kHz to 10 kHz) in a state where the tube 21 is empty. In contrast, the impedance is 160 kΩ in a state where the tube 21 is filled with the liquid. The reason why the impedance shows a low value in the state where the liquid is filled is because a conduction state is brought about between the first electrode 71 and the second electrode 72 due to the liquid within the tube 21. Additionally, it is confirmed from this experiment that there is a large difference (difference of 10 times or more) in impedance between both the state where the tube 21 is empty and the state where the tube 21 is filled with the liquid.

In a state where there is the 3-mm bubble in the tube 21, the impedance is equal to or higher than 10 MΩ. It is believed that the reason why the impedance in a state where there is the 3-mm bubble in the tube 21 is approximately equal to the impedance in a state where the tube 21 is empty (equal to or higher than 10 MΩ) is because the liquids on the upstream side and downstream side of the bubble are isolated from each other due to the bubble and both of the liquids are insulated from each other due to the bubble. According to the experimental results, even in the state where the tube 21 is nearly filled with the liquid, it can be confirmed that the impedance between the first electrode 71 and the second electrode 72 changes greatly depending on the presence/absence of a bubble with such a size that the tube 21 is blocked.

The bubble determination unit 74 determines the presence/absence of a bubble on the basis of the measurement results of the impedance measuring unit 73. The bubble determination unit 74 determines there is no bubble if the impedance that is a measurement result is equal to or lower than a predetermined threshold. Additionally, the bubble determination unit 74 determines there is a bubble if the impedance that is a measurement result is higher than the predetermined threshold.

The bubble determination unit 74 outputs the determination result to the control unit of the control board 15. The control unit continues the fixed amount transport processing (S006) when it is determined that there is no bubble, and stops the fixed amount transport processing and notifies the user of warning with sound, light, or the like when it is determined that there is a bubble.

As described above, the liquid transport apparatus of the present embodiment includes the tube 21 for transporting the liquid, the plural fingers 22 that push and block the tube, and the cam 11 that pushes the fingers in sequence so that the tube is squeezed to transport the liquid. In the case of the liquid transport apparatus 1 having such a configuration, minute bubbles generated in plural places with the operation of the respective fingers 22 are integrated, a bubble with such a size that the tube 21 is blocked is generated, and the liquids on the upstream side and downstream side of the bubble is brought into an insulated state. Using this, the liquid transport apparatus 1 of the present embodiment further includes the first electrode 71 and the second electrode 72 that are provided at the tube 21 located further toward the downstream side than the region pushed by the plural fingers 22, and the determination unit 74 that determines the presence/absence of a bubble on the basis of the impedance between the first electrode 71 and the second electrode 72, and is thereby enabled to monitor the bubble.

In addition, in the present embodiment, water-repellent treatment is performed on the inner peripheral surface of the tube 21. Accordingly, a liquid film is not easily formed between the inner peripheral surface of the tube 21 and a bubble, and the liquids on the upstream side and downstream side of the bubble is easily brought into an insulated state. For this reason, by performing the water-repellent treatment on the inner peripheral surface of the tube 21, a change in impedance during generation of a bubble become large and the bubble is easily detected.

Additionally, in the present embodiment, an alternating voltage is applied in a state where a DC component of a supply voltage of the impedance measuring unit 73 is cut so that a bias voltage is not applied between the first electrode 71 and the second electrode 72. This is because, if a DC voltage is applied between the first electrode 71 and the second electrode 72, an electrochemical process occurs in the liquid (liquid between the first electrode 71 and the second electrode 72) that comes in contact with the electrodes, a possibility that the characteristics of the liquid may change or precipitate may adhere to the electrodes occurs.

The above monitoring device 70 can be used not only for the determination of the presence/absence of a bubble but also for the determination (determination of completion of the priming processing) on whether or not the aforementioned priming processing is sufficient. For example, when the user ends the priming processing before the determination of "absence of bubble" is obtained after the start of priming, the control unit may determine that the priming processing is insufficient and notify the user of warning. This is because the bubble determination unit continues outputting the determination of "presence of bubble" since the tube is in an empty state before the start of priming, and the bubble determination unit should determine "absence of bubble" in a state where the priming processing is normally completed.

Others

The embodiment is merely for facilitating the understanding of the invention and is not intended to limit the interpretation of the invention. It is apparent that the invention may be modified and improved without departing from the spirit thereof and equivalents thereof are included in the invention.

Monitoring Device 70

In the aforementioned monitoring device 70, the impedance measuring unit 73 measures the value of the impedance between the first electrode 71 and the second electrode 72 with high precision, and the bubble determination unit 74 determines the presence/absence of a bubble on the basis of the value of the impedance. However, it is also acceptable if the value of the impedance is not measured with high precision.

For example, the impedance measuring unit may be configured so that an L-level (or H-level) signal is output when the impedance between the first electrode 71 and the second electrode 72 is equal to or lower than a predetermined value, and an H-level (or L-level) signal is output when the impedance is higher than the predetermined value, and the bubble determination unit 74 may determine the presence/absence of a bubble on the basis of the output signal of the impedance measuring unit.

Electrode

Although the aforementioned second electrode 72 serves also as the discharge-side joint 232, the second electrode is not limited to this. For example, the second electrode 72 may be constituted by a member different from the discharge-side joint 232. In this case, however, members (the first electrode 71, the second electrode 72, and the discharge-side joint 232) attached to the tube located further toward the downstream side than the region pushed by the fingers will increase.

Additionally, the above-mentioned first electrode 71 and second electrode 72 are constituted by conductive metal joints, and come into direct contact with the liquid. For example, the electrodes may be provided outside the tube and the electrodes may not come into direct contact with the liquid. In this case, however, the electrodes and the liquid are capacitively coupled to each other, and an error is easily caused when the impedance is measured.

Figure 16:
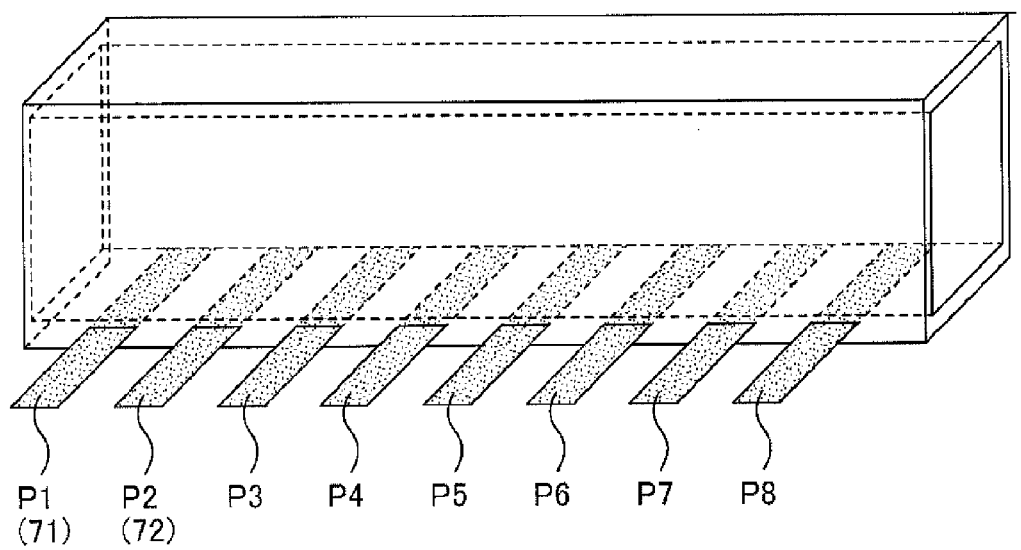
FIG. 16 is an explanatory view of another embodiment.
Figure 17A:
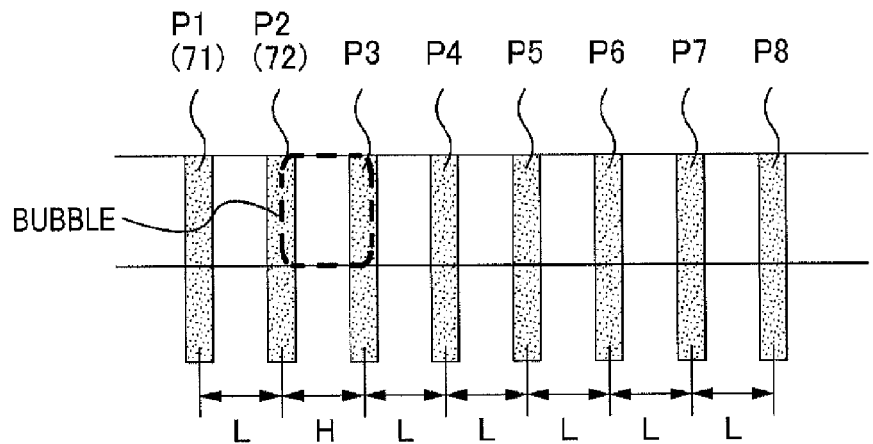
FIGS. 17A and 17B are explanatory views of determination of bubble size.
Figure 17B:
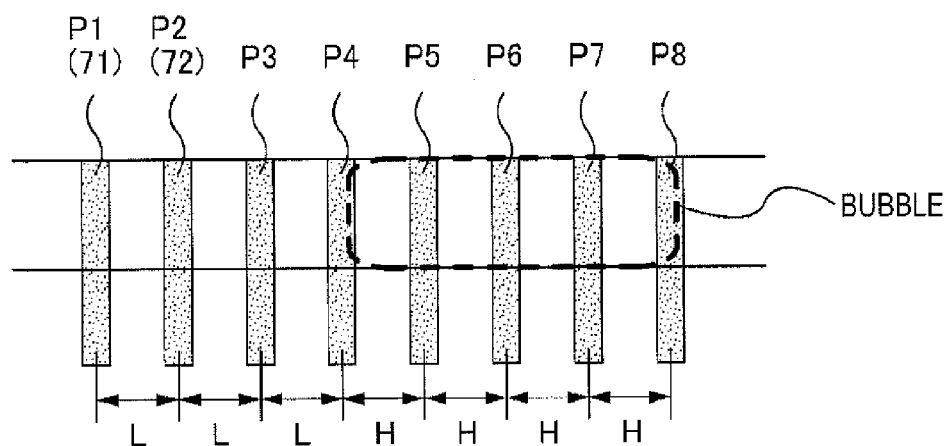

Additionally, the third electrode separate from the first electrode 71 and the second electrode 72 may be further provided, and the bubble determination unit 74 may determine the size of a bubble on the basis of the impedance between the first electrode 71 and the second electrode 72 and the impedance between two electrodes separate from these first and second electrodes. For example, as shown in FIG. 16, a flow channel having a rectangular cross-section may be formed exclusively for bubbles, and ladder electrodes P1 to P8 may be configured. In addition, the electrode P1 that constitutes the ladder electrodes is equivalent to the first electrode, the electrode P2 is equivalent to the second electrode, and the other electrodes are equivalent to the third electrode. FIGS. 17A and 17B are explanatory views of bubble size determination using the ladder electrodes of FIG. 16. "L" in the drawings indicates that the impedance between the electrodes is low, and "H" in the drawings indicates that the impedance between the electrodes is high. As shown in FIG. 17A, when the bubble size is small, only the impedance between certain adjacent electrodes (for example, electrodes P2 and P3) becomes high, and the impedance between other electrodes becomes low. On the other hand, as shown in FIG. 17B, when the bubble size is large, the impedance between the electrodes becomes high in plural continuous sections. The bubble determination unit 74 can determine the size of bubbles using this fact.

Figure 18:
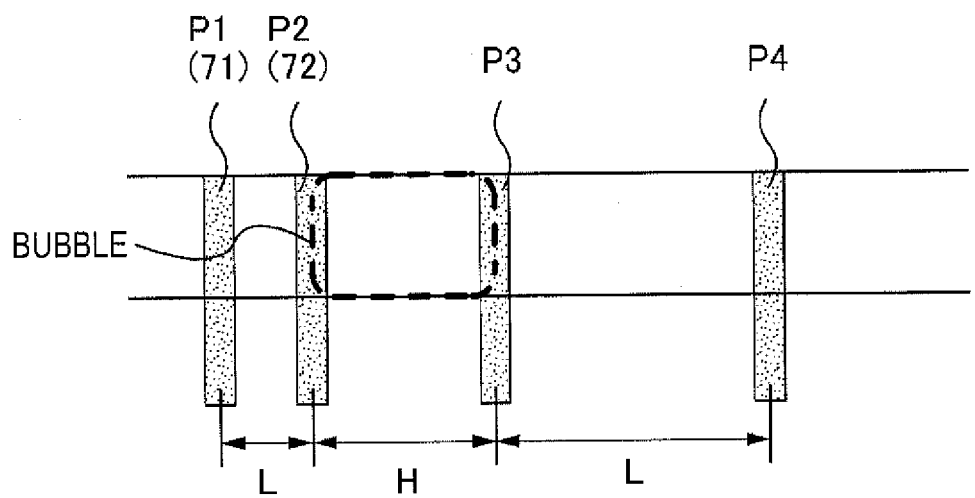
FIG. 18 is an explanatory view of still another embodiment.

Moreover, although the electrodes may be formed at equal intervals, as shown in FIG. 18, the electrodes may be provided at unequal intervals, such as a logarithmic ratio. If the bubble size can be determined in this way, when a bubble having an allowable size is detected by presetting, warning is not emitted, and when a bubble exceeding the allowable size is detected, warning can be notified of and the usability of a product improves further.

The entire disclosure of Japanese Patent Application No. 2012-239399, filed Oct. 30, 2012 is expressly incorporated by reference herein.

What is claimed is:

1. A liquid transport apparatus comprising:
    a tube that transports a liquid;
    a plurality of fingers that push and block the tube;
    a cam that pushes the fingers in sequence so as to squeeze the tube to transport the liquid;
    a first electrode and a second electrode that are provided at the tube located downstream of a region pushed by the plurality of fingers; and
    a determination unit that determines presence/absence of a bubble in the liquid transported through the tube based on an impedance between the first electrode and the second electrode.

2. The liquid transport apparatus according to claim 1, wherein water-repellent treatment is performed to an inner surface of the tube.

3. The liquid transport apparatus according to claim 1, wherein an alternating voltage is applied to the first electrode and the second electrode when the impedance between the first electrode and the second electrode is measured.

4. The liquid transport apparatus according to claim 1, wherein in a priming process of filling a flow channel of the liquid transport apparatus with the liquid, it is determined that the priming process is not completed if it is detected that the bubble is present.

5. The liquid transport apparatus according to claim 1, further comprising:
    a third electrode,
    wherein the determination unit determines a size of the bubble based on the impedance between the first electrode and the second electrode and an impedance between the first electrode and the third electrode or an impedance between the second electrode and the third electrode.

6. A bubble determination method of a liquid transport apparatus including a tube that transports a liquid, a plurality of fingers that push and block the tube, a cam that pushes the fingers in sequence so as to squeeze the tube to transport the liquid, and a first electrode and a second electrode that are provided at the tube, the method comprising:
   measuring an impedance between the first electrode and the second electrode; and
   determining presence/absence of a bubble in the liquid transported through the tube based on the measured impedance.

* * * * *